(12) United States Patent
Zhong et al.

(10) Patent No.: US 12,115,068 B2
(45) Date of Patent: Oct. 15, 2024

(54) PROTECTION AND LOADING DEVICE FOR INTERVENTIONAL VALVE SYSTEM

(71) Applicant: KINGSTRONBIO (CHANGSHU) CO., LTD, Jiangsu (CN)

(72) Inventors: Shengping Zhong, Jiangsu (CN); Chunwang Meng, Jiangsu (CN); Bo Zhang, Jiangsu (CN)

(73) Assignee: KINGSTRONBIO (CHANGSHU) CO., LTD, Jiangsu (CN)

(*) Notice: Subject to any disclaimer, the term of this patent is extended or adjusted under 35 U.S.C. 154(b) by 548 days.

(21) Appl. No.: 17/627,764

(22) PCT Filed: May 13, 2019

(86) PCT No.: PCT/CN2019/086568
§ 371 (c)(1),
(2) Date: Jan. 17, 2022

(87) PCT Pub. No.: WO2020/186609
PCT Pub. Date: Sep. 24, 2020

(65) Prior Publication Data
US 2022/0280294 A1   Sep. 8, 2022

(30) Foreign Application Priority Data
Mar. 15, 2019   (CN) .......................... 201920331042.1

(51) Int. Cl.
A61F 2/24   (2006.01)
A61F 2/966   (2013.01)
A61M 39/10   (2006.01)

(52) U.S. Cl.
CPC ............ *A61F 2/2436* (2013.01); *A61F 2/243* (2013.01); *A61F 2/966* (2013.01); *A61M 39/1011* (2013.01); *A61F 2230/0067* (2013.01)

(58) Field of Classification Search
CPC ........ A61F 2/2436; A61F 2/243; A61F 2/966; A61F 2230/0067; A61M 39/1011
See application file for complete search history.

(56) References Cited

U.S. PATENT DOCUMENTS

2007/0239271 A1*  10/2007  Nguyen ................ A61F 2/9525
                                                             623/2.11
2013/0116771 A1    5/2013  Robinson
                            (Continued)

FOREIGN PATENT DOCUMENTS

CN    101460115 A    6/2009
CN    104586542 A    5/2015
                (Continued)

OTHER PUBLICATIONS

International Search Report for corresponding PCT Application No. PCT/CN2019/086568, mailed Dec. 3, 2019.
(Continued)

*Primary Examiner* — Christopher J. Besler
(74) *Attorney, Agent, or Firm* — Tarolli, Sundheim, Covell & Tummino LLP

(57) ABSTRACT

A protection and loading device for an interventional valve system is provided. The interventional valve system includes a valve and a delivery system. The valve is fixed on a distal rod body of the delivery system. The protection and loading device includes: a first protector, a second protector, and a third protector. The first protector is located at a front end of the distal rod body and encompasses a half of the valve. The third protector is configured to fix and sleeve on the distal rod body. In a protection state, the first protector cooperates with the third protector at the first position. In a state of valve loading the first protector cooperates with the third protector at the second position.

9 Claims, 4 Drawing Sheets

(56) References Cited

U.S. PATENT DOCUMENTS

| | | |
|---|---|---|
| 2013/0190859 A1 | 7/2013 | Hillukka |
| 2014/0144000 A1 | 5/2014 | Creaven et al. |
| 2014/0331475 A1 | 11/2014 | Duffy et al. |
| 2015/0081011 A1 | 3/2015 | Young et al. |

FOREIGN PATENT DOCUMENTS

| | | |
|---|---|---|
| CN | 106361467 A | 2/2017 |
| CN | 108348270 A | 7/2018 |
| CN | 108464877 A | 8/2018 |

OTHER PUBLICATIONS

Extended European Search Report for corresponding application No. EP19920318 mailing date Sep. 15, 2023, pp. 1-9.

* cited by examiner

PROTECTION AND LOADING DEVICE FOR INTERVENTIONAL VALVE SYSTEM

CROSS-REFERENCE TO RELATED APPLICATION

The present application is a national stage of International Application No. PCT/CN2019/086568, filed on May 13, 2019, which claims priority to Chinese Patent Application No. 201920331042.1, filed on Mar. 15, 2019, and entitled with "PROTECTION AND LOADING DEVICE FOR INTERVENTIONAL VALVE SYSTEM" Both of the aforementioned applications are incorporated herein by reference in their entireties.

TECHNICAL FIELD

The present disclosure relates to the field of medical devices, and particularly, to a protection and loading device for an interventional valve system.

BACKGROUND

In the interventional valve systems of the related art, valves are currently mainly divided into two categories according to the storage manner of the valve, i.e., wet valves stored in a special preservation solution, and dry valves processed with a special dry treatment. The dry valves are further divided into preoperative installation on site and pre-mounted (full-loading or half-loading). After demonstration, the manufacturer's half-loading pre-mounted valve system has obvious advantages compared with other valve systems. However, meanwhile, the half-loading pre-mounted valve system of the manufacturer puts forward higher requirements for the devices for matched protection and the devices used for on-site installation.

Therefore, it is necessary to design a protection and loading device with a simple structure and simplified operation.

SUMMARY

The present disclosure provides a protection and loading device for an interventional valve system to solve the problems in the related art and simplify operation.

The present disclosure provides a protection and loading device for an interventional valve system. The interventional valve system includes a valve and a delivery system. The valve is fixed on a distal rod body of the delivery system through a connecting device of the delivery system. The protection and loading device includes: a first protector and a second protector that are cooperating with each other; and a third protector configured to fix on and sleeve on the distal rod body. The first protector is located at a side close to the distal rod body and encompasses at least a half of the valve. In a protection state, the first protector cooperates with the third protector at a first position. In a state of valve loading, the first protector cooperates with the third protector at a second position, where the second position is farther away from the valve than the first position.

In an embodiment, the first protector includes a first large-diameter portion, a first conical portion, and a first small-diameter portion that are arranged in sequence; the second protector includes a second large-diameter portion, a second conical portion, and a second small-diameter portion that are arranged in sequence; the first large-diameter portion cooperates with the second large-diameter portion; and the first small-diameter portion cooperates with the third protector.

In an embodiment, the third protector includes a sleeve and a locking member; the sleeve has a first end sleeved on and fixed on the first small-diameter portion; and the distal rod body includes a thick rod and a thin rod, the sleeve is sleeved on the thick rod, and the locking member cooperates with a first step formed between the thick rod and the thin rod, and is sleeved on and fixed to a second end of the sleeve.

In an embodiment, the sleeve includes a body and a grasping portion; and a second step is formed between the body and the grasping portion, and the second step serves as the second position in the state of valve loading.

In an embodiment, the grasping portion has an outer surface with knurling.

In an embodiment, the sleeve is provided with a ventilation hole.

In an embodiment, the sleeve has an outer wall provided with a limiting groove; the first small-diameter portion has an inner wall provided with a limiting block; and the limiting block cooperates with the limiting groove at the first position.

In an embodiment, the limiting groove includes a vertical groove opened along the axial direction of the sleeve, and a horizontal groove perpendicular to the vertical groove; and the limiting block cooperates with an end of the horizontal groove away from the vertical groove at the first position.

In an embodiment, the locking member includes an upper fixing portion and a lower fixing portion; the upper fixing portion includes a first half-conical tube and a first head; and the lower fixing portion includes a second half-conical tube and a second head; the first half-conical tube and the second half-conical tube are snapped with each other, and then extend into the sleeve from the second end of the sleeve; and the first head and the second head are snapped with each other, and then are sleeved on the thin rod, and cooperate with the first step formed between the thick rod and the thin rod.

In an embodiment, the first head is provided with at least one of an upper limiting hole or an upper limiting post; the second head is provided with at least one of a lower limiting hole or a lower limiting post; and the upper limiting hole cooperates with the lower limiting post; and the lower limiting hole cooperates with the upper limiting post.

The technical solutions provided by the present disclosure can achieve the following beneficial effects.

The protection and loading device for the interventional valve system provided by the present disclosure includes the first protector, the second protector, and the third protector. The first protector and the second protector can be snapped with each other to form an accommodating cavity. The first protector is located at the side close to the distal rod body of the delivery system, and encompasses at least a half of the valve. The third protector is configured to fix on and sleeve on the distal rod of the delivery system. In the protection state, the first protector cooperates with the third protector at the first position. In the state of valve loading, the first protector cooperates with the third protector at the second position. With the above structure, it is realized that the valve is protected when being transported. When loading the valve, the valve can be loaded only by changing the relative position between the first protector and the third protector, squeezing the valve by the second protector, and cooperating with the loading action of the delivery system, thereby simplifying the operation, and achieving a simpler structure of the whole device.

It should be understood that the above general description and the following detailed description are only exemplary, which cannot limit the present disclosure.

BRIEF DESCRIPTION OF DRAWINGS

In order to more clearly illustrate technical solutions of embodiments of the present disclosure or the technical solutions in the related art, the accompanying drawings used in the embodiments or the related art are briefly described below. The drawings described below are merely a part of the embodiments of the present disclosure. Based on these drawings, those skilled in the art can obtain other drawings without any creative effort.

REFERENCE SIGNS

Figure 1:
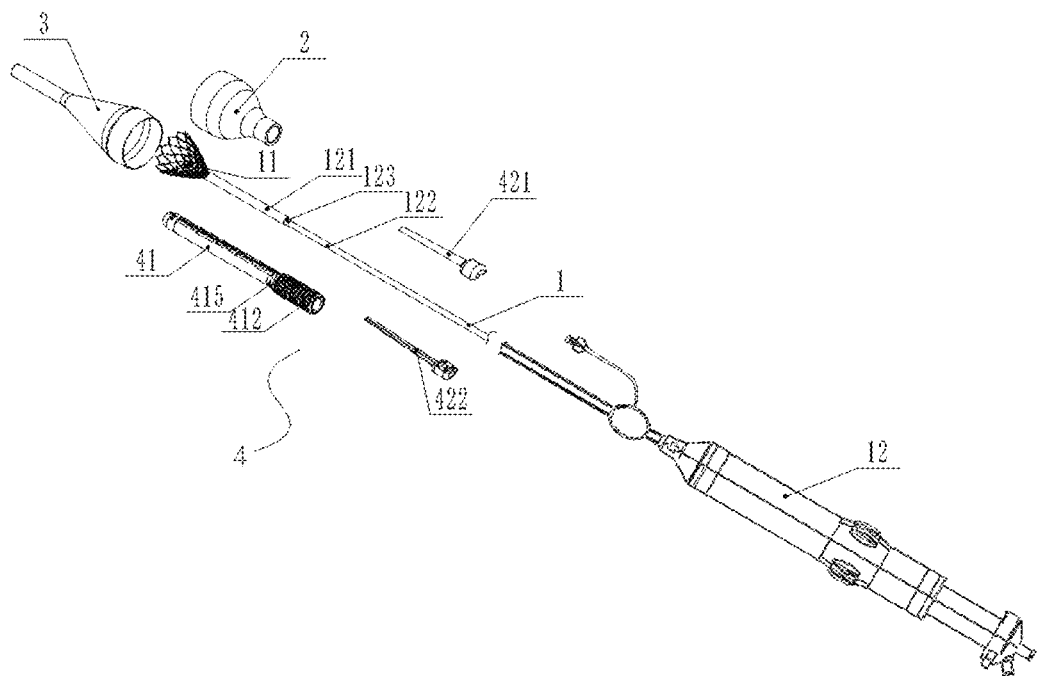
FIG. 1 is an exploded view of a protection and loading device for an interventional valve system according to an embodiment of the present disclosure.

- 1—interventional valve system;
  - 11—valve;
  - 12—distal rod body;
    - 121—thick rod;
    - 122—thin rod;
    - 123—first step;
- 2—first protector;
  - 21—first large-diameter portion;
  - 22—first conical portion;
  - 23—first small-diameter portion;
  - 24—limiting block;
- 3—second protector;
  - 31—second large-diameter portion;
  - 32—second conical portion;
  - 33—second small-diameter portion;
  - 34—cone surface;
- 4—third protector;
  - 41—sleeve;
    - 411—body;
    - 412—grasping portion;
    - 413—ventilation hole;
    - 414—limiting groove;
    - 415—second step;
    - 416—conical hole;
  - 42—locking member;
    - 421—upper fixing portion;
    - 421*a*—first half-conical tube;
    - 421*b*—first head;
    - 422—lower fixing portion;
    - 422*a*—second half-conical tube;
    - 422*b*—second head;
    - 422*c*—lower limiting hole;
    - 422*d*—lower limiting post.

DESCRIPTION OF EMBODIMENTS

The technical solutions of the present disclosure will be clearly and completely described below in conjunction with the accompanying drawings. The described embodiments are merely part of the embodiments of the present disclosure rather than all of the embodiments. All other embodiments obtained by those skilled in the art based on the embodiments of the present disclosure without paying creative labor shall fall into the protection scope of the present disclosure.

In the description of the present disclosure, it should be noted that the orientation or positional relationships indicated by the terms "inner", "outer", and the like are based on the orientation or positional relationship shown in the drawings, which is only for the convenience of describing the present disclosure and simplifying the description, and does not indicate or imply that the mentioned device or element has a specific orientation, be configured and operated in a particular orientation, and therefore cannot be understood as a limitation to the present disclosure.

In the description of the present disclosure, it should be noted that, unless otherwise clearly specified and limited, the terms "installation", "interconnection", and "connection" should be understood in a broad sense, for example, it can be a fixed connection, a detachable connection or an integral connection; it can be a mechanical connection or an electrical connection; it can be a direct connection or indirect connection through an intermediate medium, and it can be internal communication between two components. For those skilled in the art, the specific meaning of the above-mentioned terms in the present disclosure can be understood under specific circumstances.

As shown in FIG. 1, an embodiment of the present disclosure provides a protection and loading device for an interventional valve system 1. The interventional valve system 1 includes a valve 11 and a delivery system. The valve 11 is fixed to a first end of a distal rod body 12 of the delivery system through a connecting device of the delivery system.

The protection and loading device includes a first protector 2, a second protector 3, and a third protector 4. The first protector 2 and the second protector 3 can be opposite to each other and cooperate with each other. The first protector 2 is located at a side close to the distal rod body 12 and encompasses at least a half of the valve 11. The third protector 4 is configured to be fixed on and sleeved on the distal rod body 12.

Figure 7:
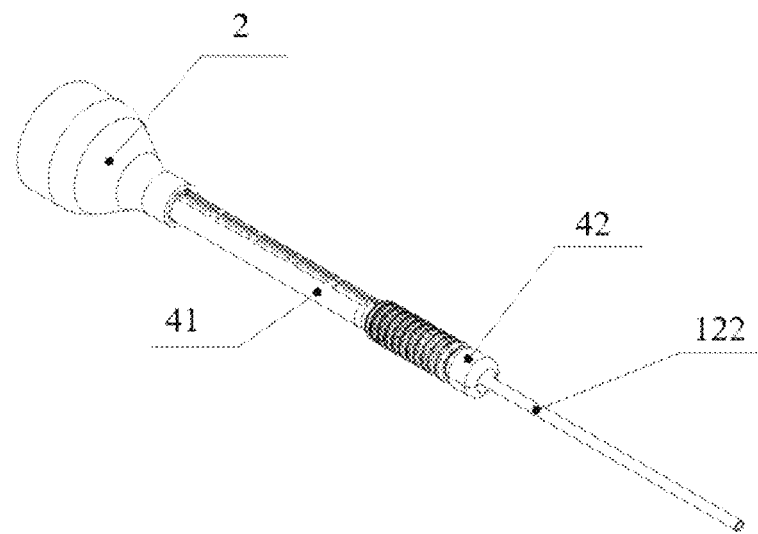
FIG. 7 is a schematic diagram showing a state of a protection and loading device for an interventional valve system when it is in a first position, according to an embodiment of the present disclosure.

In a protection state, the first protector 2 cooperates with the third protector 4 at a first position (referring to FIG. 7). In a state of valve loading 11, the first protector 2 cooperates with the third protector 4 at a second position (referring to FIG. 8). The second position is farther away from the valve 11 than the first position.

In an embodiment, the overall first protector 2 is a hollow structure with two opened ends, and the overall second protector 3 is also a hollow structure with two opened ends. The first protector 2 and the second protector 3 are snapped with each other to form an accommodating cavity. During transportation, the first protector 2 can protect the valve 11. However, after the first protector 2 cooperates with the second protector 3, the valve 11 is protected better.

The third protector 4 is hollow and open at both ends, and can cooperate with the first protector 2. During the transportation, the first protector 2 cooperates with the third protector 4 at the first position, so that the first protector 2 protects the valve 11, and the third protector 4 protects the distal rod body 12. When the valve 11 is to be loaded after the transportation, the first protector 2 cooperates with the third protector 4 at the second position, so that the second protector 3 can squeeze the valve 11 to deform the valve 11. Accompanied by a loading action of the distal rod body 12, the valve 11 can be completely loaded into the distal rod body 12 to reach a usage state.

Figure 2:
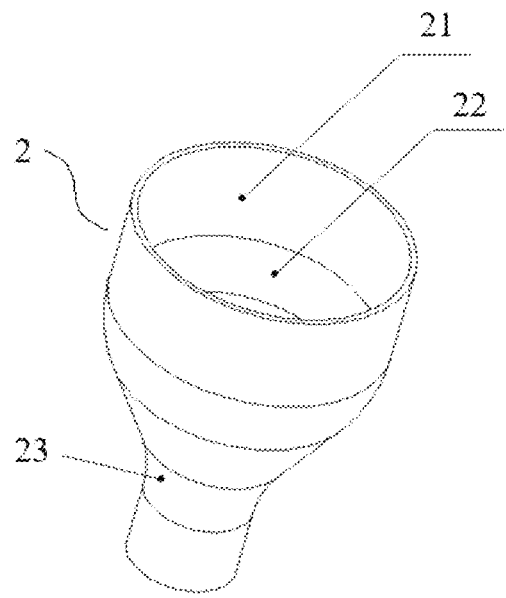
FIG. 2 is a schematic diagram of a first protector from one perspective.
Figure 3:
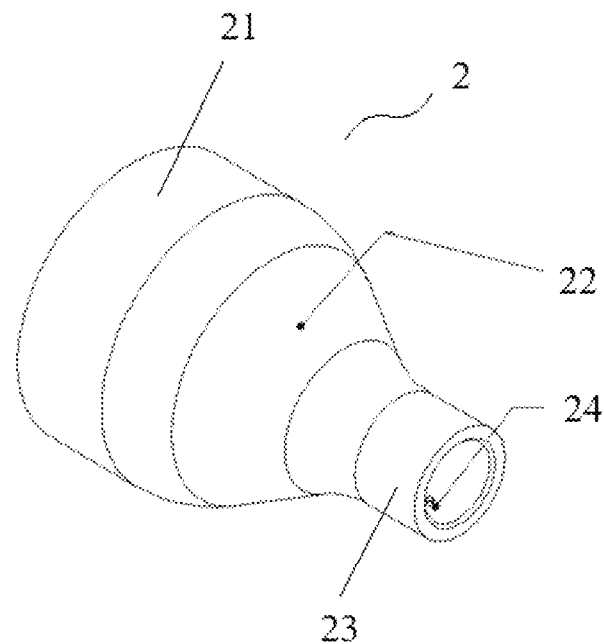
FIG. 3 is a structural schematic diagram of a first protector from another perspective.

In an embodiment, as shown in FIG. 2 and FIG. 3, the first protector 2, as a whole, has a substantially funnel shape, and includes a first large-diameter portion 21, a first conical portion 22, and a first small-diameter portion 23 that are sequentially arranged. The first large-diameter portion 21 can have a certain taper. The first small-diameter portion 23 has a cylindrical shape. The first conical portion 22 is located between the first large-diameter portion 21 and the first small-diameter portion 23.

Figure 4:
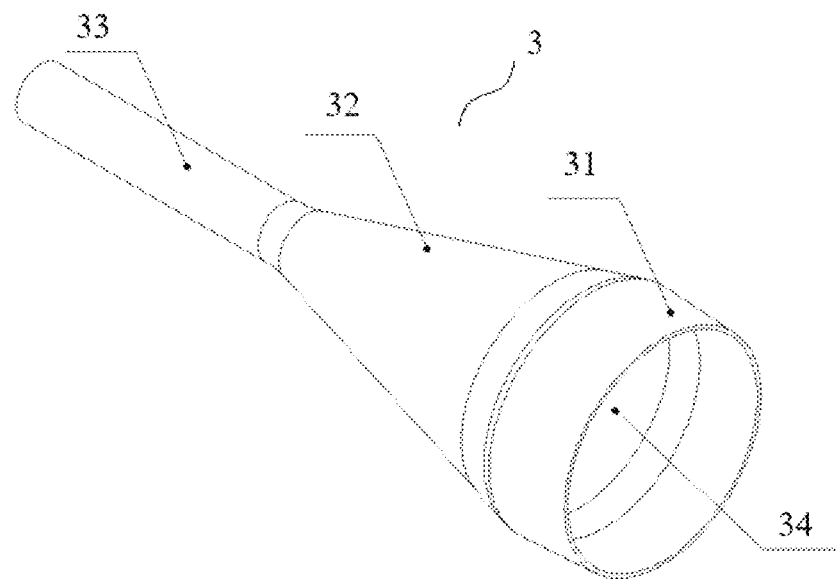
FIG. 4 is a schematic diagram of a second protector.

As shown in FIG. 4, the second protector 3, as a whole, has a substantially funnel shape, and includes a second large-diameter portion 31, a second conical portion 32, and a second small-diameter portion 33 that are sequentially arranged. The second large-diameter portion 31 has a same taper as the first large-diameter portion 21, so as to cooperate with the first large-diameter portion 21. The second small-diameter portion 33 has a cylindrical shape. The second conical portion 32 is located between the second large-diameter portion 31 and the second small-diameter portion 33. An inner wall surface of the second conical portion 32 forms a conical surface 34 for squeezing the valve 11.

The first large-diameter portion 21 and the second large-diameter portion 31 are butted and snapped with each other to form an accommodating cavity for protecting the valve 11, and the first small-diameter portion 23 cooperates with the third protector 4.

Figure 5:
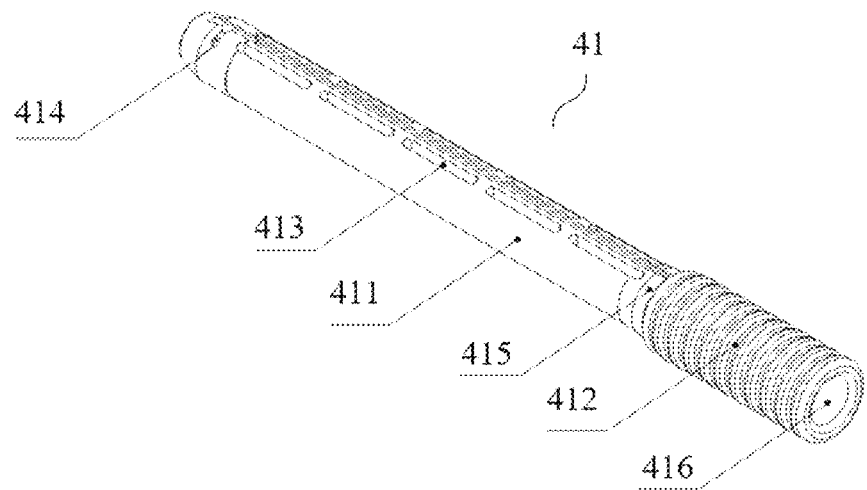
FIG. 5 is a schematic diagram of a sleeve in a third protector.
Figure 6:
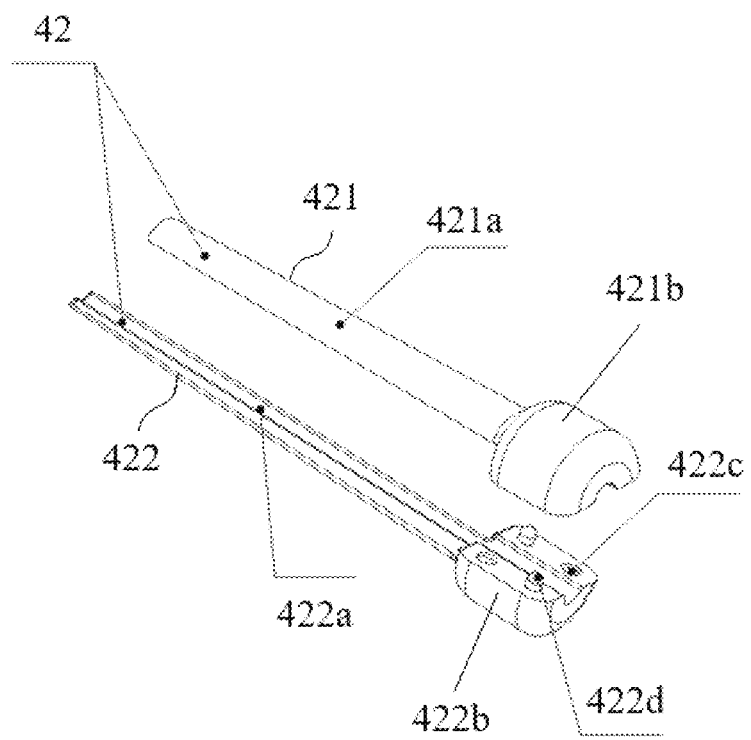
FIG. 6 is a exploded view of a locking member in a third protector.

As shown in FIG. 5 and FIG. 6, in an embodiment, the third protector 4 includes a sleeve 41 and a locking member 42. A first end of the sleeve 41 is sleeved and fixed on the first small-diameter portion 23. The distal rod body 12 includes a thick rod 121 and a thin rod 122. The sleeve 41 is sleeved on the thick rod 121. The locking member 42 cooperates with a first step 123 formed between the thick rod 121 and the thin rod 122, and is sleeved and fixed on a second end of the sleeve 41. In this way, the sleeve 41 can protect a part of the distal rod body 12 (thick rod 121) of the interventional valve system 1, and the locking member 42 can lock the sleeve 41.

Further, the sleeve 41 includes a body 411 and a grasping portion 412. A second step 415 is formed between the body 411 and the grasping portion 412. In a loading state of the valve 11, the second step 415 serves as the second position. When the valve 11 is to be loaded, the first protector 2 is slid to the second position relative to the outer wall of the sleeve 41. Since the second protector 3 is snapped and fixed with the first protector 2, the second protector 3 can squeeze the valve 11 during the sliding process, so that the valve 11 is deformed to be loaded into the thick rod 121.

In an embodiment, an outer surface of the grip portion 412 is provided with knurling to facilitate operator to grasp.

The sleeve 41 is also in an embodiment provided with a ventilation hole 413. The interventional valve system 1 is sterilized by providing the ventilation hole 413. The ventilation hole 413 can be a long strip hole, a round hole, or other profiled hole, and is opened on the sleeve 41 along an axis of the sleeve 41. It can be understood by those skilled in the art that the number of ventilation holes 413 can be one or more, and can be set according to actual conditions.

As mentioned above, in the transportation state, the first protector 2 cooperates with the third protector 4 in the first position. The implementation of the first position can be realized in following ways. The outer wall of the sleeve 41 is opened with a limiting groove 414. An inner wall of the first small-diameter portion 23 is provided with a limiting block 24 (referring to FIG. 3). The limiting block 24 cooperates with the limiting groove 414 at the first position. When the valve is to be in the storage state after the transportation, the first protector 2 is slid along the sleeve 41 of the third protector 4 to be in the second state, so that the second protector 3 squeezes the valve 11 to load it inside the sleeve 41.

Specifically, the limiting groove 414 includes a vertical groove opened along an axial direction of the sleeve 41 and a horizontal groove perpendicular to the vertical groove. The limiting block 24 cooperates with an end of the horizontal groove away from the vertical groove at the first position.

In the transportation state, the limiting block 24 cooperates with the farthest end of the horizontal groove to lock. When loading is performed on-site before surgery, the first protector 2 is rotated so that the limiting block 24 slides into the vertical groove along the horizontal groove, at this time, the first protector 2 is released from the sleeve 41. Subsequently, the first protector 2 is pushed to slide along the vertical groove to the second step 415 located between the sleeve 41 and the locking member 42, and is limited by the second step 415 to reach the second position. During the sliding process of the first protector 2 along the vertical groove, the second protector 3 squeezes the valve 11 to be deformed and loaded in the sleeve 41.

Figure 8:
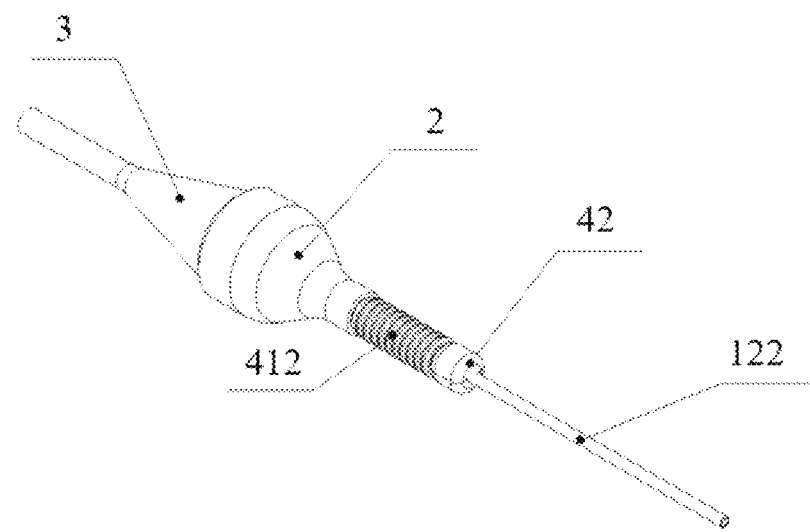
FIG. 8 is a schematic diagram showing a state of a protection and loading device for an interventional valve system when it is in a second position, according to an embodiment of the present disclosure.

FIG. 7 shows a state where the first protector 2 cooperates with the third protector 4 at the first position, and this state is a transportation state where the device plays a protective role. As shown in FIG. 8, the first protector 2 cooperates with the third protector 4 at the second position, and such state is the loading state where the device loads the valve 11.

As shown in FIG. 6, the locking member 42 can include an upper fixing portion 421 and a lower fixing portion 422. The structures of the upper fixing portion 421 and the lower fixing portion 422 can be the same or different from each other. This embodiment takes that the upper fixing portion 421 and the lower fixing portion 422 have a same structure as an example for description. The upper fixing portion 421 includes a first half-conical tube 421*a* and a first head 421*b*. The lower fixing portion 422 includes a second half-conical tube 422*a* and a second head 422*b*. The first half-conical tube 421*a* and the second half-conical tube 422*a* are snapped with each other, and then extend into the sleeve 41 from the second end of the sleeve 41. A conical hole 416 is provided at an end of the grasping portion 412 of the sleeve 41 away from the body 411 (referring to FIG. 5). An outer wall surface obtained by snapping the first half-conical tube 421*a* and the second half-conical tube 422*a* has a conical shape, which can cooperate with the conical hole 416.

The first head 421*b* and the second head 422*b* are snapped with each other to be sleeved on the thin rod 122, and cooperates with the first step 123 located between the thick rod 121 and the thin rod 122.

There are many ways to fix the upper fixing portion 421 and the lower fixing portion 422. In an embodiment, at least one of an upper limiting hole or an upper limiting post are provided on the first head 421*b*. The second head 422*b* is provided with at least one of a lower limiting hole 422*c* or a lower limiting post 422*d*. The upper limiting hole cooperates with the lower limiting post 422d, and the lower limiting hole 422c cooperates with the upper limiting post.

The above limiting hole can be a blind hole. The limiting post can be a cylindrical shape, and has a chamfer on its top. The limiting hole and the limiting post cooperate with each other to realize fixation between the upper fixing portion 421 and the lower fixing portion 422.

Finally, when the overall device is to be detached, the locking member 42 is drawn out, and the other components lose their fastening force and can be drawn out in a direction opposite to the drawing lock member 42.

It can be understood by those skilled in the art that the locking cooperation manner between the locking member 42 and the sleeve 41 is not limited to the above cooperation manner, and other manners such as threaded connection or snapping connection can also be adopted.

The above embodiments of the present disclosure are several preferred embodiments, but not intended to limit the scope of the claims. Various changes and modifications can be made by those skilled in the art without departing from the scope of the present application. Any modification, equivalent replacement, improvement, and the like made within the spirit and principle of the present disclosure shall be included in the protection scope of the present disclosure.

What is claimed is:

1. A protection and loading device for an interventional valve system, comprising:
    a first protector and a second protector that are capable of cooperating with each other, wherein the interventional valve system comprises a valve and a delivery system, wherein the valve is fixed on a distal rod body of the delivery system; and the first protector is configured to be located at a side close to the distal rod body and encompasses at least a half of the valve, and wherein the first protector comprises a first large-diameter portion, a first conical portion, and a first small-diameter portion that are arranged in sequence, the second protector comprises a second large-diameter portion, a second conical portion, and a second small-diameter portion that are arranged in sequence; and
    a third protector configured to fix on and sleeve on the distal rod body, wherein the third protector comprises a sleeve and a locking member that comprises an upper fixing portion and a lower fixing portion; wherein the upper fixing portion comprises a first half-conical tube and a first head; the lower fixing portion comprises a second half-conical tube and a second head; the first half-conical tube and the second half-conical tube are snapped with each other, and then extend into the sleeve from thea second end of the sleeve; and the first head and the second head are snapped with each other;
    wherein the protection and loading device is configured for use and to be moved to a protection state, the first protector cooperates with the third protector at a first position; and
    wherein the protection and loading device is configured for use and to be moved to a state of valve loading, the first protector and the second protector are snapped with each other, and the first protector cooperates with the third protector at a second position while the second protector squeezes the valve, to assist a loading action of the delivery system to complete a loading of the valve, wherein the second position is farther away from the valve than the first position.

2. The protection and loading device according to claim 1, wherein the first large-diameter portion cooperates with the second large-diameter portion, and the first small-diameter portion cooperates with the third protector.

3. The protection and loading device according to claim 2, wherein
    the sleeve has a first end inserted in and fixed on the first small-diameter portion; and
    the distal rod body comprises a thick rod and a thin rod, wherein the sleeve is configured to be sleeved on the thick rod, and the locking member is configured to cooperate with a first step formed between the thick rod and the thin rod, and is sleeved on and fixed to a second end of the sleeve.

4. The protection and loading device according to claim 3, wherein the sleeve comprises a body and a grasping portion, wherein the grasping portion comprises an outer surface with knurling, a second step is formed between the body and the grasping portion, and the second step serves as the second position in the state of valve loading.

5. The protection and loading device according to claim 4, wherein the sleeve is provided with a ventilation hole.

6. The protection and loading device according to claim 4, wherein the sleeve has an outer wall provided with a limiting groove;
    the first small-diameter portion has an inner wall provided with a limiting block; and
    the limiting block cooperates with the limiting groove at the first position.

7. The protection and loading device according to claim 6, wherein the limiting groove comprises a vertical groove opened along an axial direction of the sleeve, and a horizontal groove perpendicular to the vertical groove; and
    the limiting block cooperates with an end of the horizontal groove away from the vertical groove at the first position.

8. The protection and loading device according to claim 3, wherein
    the first head and the second head are snapped with each other, and the first head and the second head are configured to be sleeved on the thin rod and cooperate with the first step formed between the thick rod and the thin rod.

9. The protection and loading device according to claim 8, wherein the first head is provided with at least one of an upper limiting hole or an upper limiting post;
    the second head is provided with at least one of a lower limiting hole or a lower limiting post;
    the upper limiting hole cooperates with the lower limiting post; and
    the lower limiting hole cooperates with the upper limiting post.

* * * * *